US010450132B2

(12) United States Patent
Heikkilä

(10) Patent No.: US 10,450,132 B2
(45) Date of Patent: Oct. 22, 2019

(54) CONTAINER SECURITY SYSTEM WITH OSCILLATION DEVICE AND METHOD FOR PERFORMING CONTAINER HANDLING USING CONTAINER SECURITY SYSTEM WITH OSCILLATION DEVICE

(71) Applicant: CONEXBIRD OY, Palokka (FI)

(72) Inventor: Teuvo Heikkilä, Palokka (FI)

(73) Assignee: CONEXBIRD OY, Palokka (FI)

(*) Notice: Subject to any disclaimer, the term of this patent is extended or adjusted under 35 U.S.C. 154(b) by 0 days.

(21) Appl. No.: 14/344,720

(22) PCT Filed: Sep. 20, 2012

(86) PCT No.: PCT/FI2012/000037
§ 371 (c)(1),
(2) Date: Mar. 13, 2014

(87) PCT Pub. No.: WO2013/045742
PCT Pub. Date: Apr. 4, 2013

(65) Prior Publication Data
US 2014/0345382 A1  Nov. 27, 2014

(30) Foreign Application Priority Data

Sep. 29, 2011  (FI) .................................. 20110332

(51) Int. Cl.
*B65D 90/48* (2006.01)
*B66C 13/16* (2006.01)
(Continued)

(52) U.S. Cl.
CPC .............. *B65D 90/48* (2013.01); *B66C 1/101* (2013.01); *B66C 13/16* (2013.01); *B66C 13/46* (2013.01);
(Continued)

(58) Field of Classification Search
CPC ......... B66C 13/16; B66C 13/46; B66C 1/101; B66C 19/002; B66C 19/005;
(Continued)

(56) References Cited

U.S. PATENT DOCUMENTS 3,504,532 A * 4/1970 Adler ..................... G01N 29/12
73/579
3,967,497 A * 7/1976 Brown ................... G01G 3/165
177/210 R
(Continued)

FOREIGN PATENT DOCUMENTS

CN       201033717 Y    3/2008
DE         224407 A *  7/1985 ............... G01N 3/32
(Continued)

OTHER PUBLICATIONS

U.S. Customs and Border Protection, Supply Chain Security Best Practices Catalog, Jan. 2006.*
(Continued)

*Primary Examiner* — Justin Seo
*Assistant Examiner* — David L Singer
(74) *Attorney, Agent, or Firm* — Oliff PLC

(57) ABSTRACT

A container security system is disclosed that includes force sensors and acceleration sensors attached to a lifting beam of a container handling device or to another part of a frame of the container handling device. The container security system also includes an electronics unit and an oscillation device attached to the lifting beam of the container handling device or to another part of the frame of the container handling device. The oscillation device creates oscillation of a container and contents of the container, and the container security system recognizes (i) a change in a condition of the
(Continued)

container or the container contents as well as (ii) a change in an amount of the container contents between different container handling stages.

16 Claims, 4 Drawing Sheets

(51) Int. Cl.
    *G01G 3/16*     (2006.01)
    *G06Q 10/08*     (2012.01)
    *B66C 1/10*     (2006.01)
    *B66C 13/46*     (2006.01)
    *B66C 19/00*     (2006.01)
    *G01N 29/12*     (2006.01)
    *G01N 29/44*     (2006.01)

(52) U.S. Cl.
    CPC ............ *B66C 19/002* (2013.01); *G01G 3/16* (2013.01); *G01N 29/12* (2013.01); *G01N 29/4427* (2013.01); *G06Q 10/08* (2013.01); *G01N 2291/014* (2013.01)

(58) Field of Classification Search
    CPC ........ B66C 19/007; G01G 3/16; B65D 90/48; G06Q 10/08; G01N 29/12; G01N 29/4427; G01N 29/06; G01N 29/0654; G01N 2291/014; G01L 35/30; G01H 13/00; G01H 13/46; G01H 1/14; G01B 5/30
    USPC .......... 73/579, 580, 582; 206/459.1; 702/56, 702/174
    See application file for complete search history.

(56) References Cited

U.S. PATENT DOCUMENTS

| | | | | |
|---|---|---|---|---|
| 4,297,884 A | * | 11/1981 | Leveque | ............ A61B 5/0051 600/587 |
| 4,370,888 A | | 2/1983 | Popper | |
| 4,596,142 A | * | 6/1986 | Poole | ............ G01N 29/12 73/579 |
| 5,245,876 A | * | 9/1993 | Jones | ............ G01N 3/32 73/579 |
| 5,533,399 A | * | 7/1996 | Gibson | ............ G01H 5/00 73/579 |
| 5,625,146 A | * | 4/1997 | Hull | ............ G01H 13/00 73/574 |
| 5,886,263 A | * | 3/1999 | Nath | ............ G01N 29/045 700/30 |
| 2003/0040885 A1 | * | 2/2003 | Schoess | ............ G01G 3/16 702/173 |
| 2003/0220556 A1 | * | 11/2003 | Porat | ............ A61B 5/0051 600/407 |
| 2003/0227382 A1 | * | 12/2003 | Breed | ............ G06Q 20/203 340/539.13 |
| 2004/0024644 A1 | * | 2/2004 | Gui | ............ G06Q 10/08 705/22 |
| 2004/0222888 A1 | * | 11/2004 | Young | ............ G06K 7/0008 340/568.1 |
| 2006/0113384 A1 | | 6/2006 | Kurita et al. | |
| 2006/0220842 A1 | | 10/2006 | Breed | |
| 2007/0006652 A1 | * | 1/2007 | Weldon, Jr. | ............ G01G 3/16 73/579 |
| 2007/0276619 A1 | | 11/2007 | Sugahara et al. | |
| 2008/0011091 A1 | * | 1/2008 | Weldon, Jr. | ............ G01L 1/255 73/766 |
| 2009/0058593 A1 | * | 3/2009 | Breed | ............ B60C 11/24 340/5.2 |
| 2010/0161254 A1 | | 6/2010 | Atlas et al. | |

FOREIGN PATENT DOCUMENTS

| | | | |
|---|---|---|---|
| JP | 07294408 A | * 11/1995 | |
| SU | 735960 A1 | * 5/1980 | |
| WO | WO-9116003 A1 | * 10/1991 | ........... A61B 5/0051 |

OTHER PUBLICATIONS

Machine Translation & Derwent Summary of DD224407A1 (Year: 2018).*
May 19, 2015 Search Report issued in European Patent Application No. 12837372.7.
Jan. 25, 2013 Search Report issued in International Patent Application No. PCT/FI2012/000037.
Jan. 25, 2013 Written Opinion issued in International Patent Application No. PCT/FI2012/000037.
Translation of Dec. 22, 2014 Office Action issued in Chinese Patent Application No. 201280048063.3.

\* cited by examiner

Fig. 4

DEPARTURE HARBOUR OSCILLATION CODE

| Code ID | Number of the container | SN1 of the container | SN2 of the container handling device | SN3 of the oscillation device | Control ID | T | A ka. | A(t) | R |
|---|---|---|---|---|---|---|---|---|---|
| 25.0 | nro123 | SN100 | SN200 | SN300 | 35 | X1 | X2 | X3 | X% |

ARRIVAL HARBOUR OSCILLATION CODE

| Code ID | Number of the container | SN1 of the container | SN2 of the container handling device | SN3 of the oscillation device | t | Control ID | T | A ka. | A(t) | R |
|---|---|---|---|---|---|---|---|---|---|---|
| 25.3 | nro123 | SN101 | SN201 | SN301 | 27 | 35 | X1 | X2 | X3 | X% |

ARRIVAL HARBOUR REFERENCE CODE

| Code ID | Number of the container | SN1 of the container | SN2 of the container handling device (departure) | SN3 of the oscillation device (departure) | SN2 of the container handling device (arrival) | SN3 of the oscillation device (arrival) | T | A ka. | A(t) | R |
|---|---|---|---|---|---|---|---|---|---|---|
| 25.4 | nro123 | SN101 | SN200 | SN300 | SN201 | SN301 | OK | OK | OK | OK |

CONTAINER SECURITY SYSTEM WITH OSCILLATION DEVICE AND METHOD FOR PERFORMING CONTAINER HANDLING USING CONTAINER SECURITY SYSTEM WITH OSCILLATION DEVICE

BACKGROUND

This invention relates to a container security system and a method for performing handling with a container security system.

In known container logistics, in the freight handling areas are performed inspection measures relating to container security to prevent travelling as a stowaway, smuggling, changing container contents to be different from the freight information or changing the condition of the container contents. Inspection measures can be scanning of an unopened container or measuring the carbon dioxide content of an unopened container from the ventilation openings of the container using a separate measuring device. Using scanning of a container, the contents of its freight can be determined, but the method is expensive. Hand-held carbon dioxide meters have usability problems in large container handling areas. Hand-held meters are suitable mainly for so-called precision inspections. As an inspection measure is also used the opening of containers. All the above said inspection measures increase the turnaround time of containers in container handling areas and require an additional process and an additional personnel resource to function. The weighing of a container is used to aid in preventing, for example, overloading, weight deviation and a so-called imbalance situation of the container. Using this method, an interpretation cannot be made regarding whether it is a question of possible travelling as a stowaway, smuggling, changing of container contents to be different from the freight information or changing of the condition of the container contents. In addition to the above, in known container logistics, a significant number of containers become damaged. It is particularly common that the producer of the damage as well as the stage, at which the damage occurred, remain unclear and the expenses of the damage cannot be collected.

SUMMARY

The object of the invention is to eliminate the above said disadvantages and to provide a container security system that does not require an expensive or separate measurement process or an additional personnel resource to perform the inspection measure of a container. Furthermore, the object of the invention is to produce an information-secure system solution.

This object can be achieved according to the invention using container handling devices (for example, a crane, straddle carrier, telehandler) such that into the container handling devices is added a system. The container inspection measure is performed using the above said container handling resources and the invented system, while the container is being moved (for example, loading, unloading, storage). Using a system according to the method, a departing container is secured with an identification (a code) produced by the system and the need for inspection (results) of a received container is determined. The result can be an indication that inside the above said container is a stowaway/stowaways. In addition to a person, the stowaway can also be an animal. Additionally, the result can also be a deviation from weight and/or contents declared in advance in the freight information or a change in the condition of the contents, or the condition of the container has changed. The container handling devices of the container handling area, described above, are coupled to the system by means of the user interfaces, software, wireless data transmission and encrypted data network connection of the invented system.

Publications US 2006/0220842 A1, US 2007/0276619 A1 and US 2006/0113384 A1 present technology used to attempt to recognize intruders into a container and a possible change in the container contents using inertia sensors (which can be force- or acceleration sensors) to be installed inside the container or in the handling devices of the container. Unlike the above publications, the technology to be followed in this invention does not require the oscillation caused by the container itself or an intruder into the container, instead the results to be presented are determined by comparing changes in the elasticity of the object (container and/or container contents) to be measured.

Publication U.S. Pat. No. 4,370,888 and publications cited in the publication present the general state of the art following the measurement based on an oscillation change of the moving mass of the object to be measured. Unlike the above publications, the technology to be followed in this invention does not require a change in the mass, instead the results to be presented are determined by comparing changes in the elasticity of the object (container and/or container contents) to be measured.

Above said elasticity and changes in the elasticity of the object to be measured are determined by measuring forced oscillation using acceleration- and force sensors installed in a container handling device and by analysing the measurement results in the electronics unit of the apparatus. The forced oscillation of the container and the container handling device is produced programmatically by stimulating with an oscillation device attached to the container handling device.

More specifically, a container security system according to the invention is characterized by force sensors and acceleration sensors to be attached to a so-called lifting beam of a container handling device or to some other part of a frame of the container handling device, an electronics unit of the system, an oscillation device, wherein the oscillation device is attached to the so-called lifting beam of the container handling device or to some other part of the frame of the container handling device, and the oscillation device creates oscillation of the container and the container contents, and that the system recognizes a change in a condition of the container or container contents as well as a change in an amount of the container contents between different container handling stages.

BRIEF DESCRIPTION OF THE DRAWINGS

In the following, the invention is described in more detail with reference to the accompanying drawings, which as a partial depiction of the system present a system according to the invention.

FIG. 4 shows methods of a system according to the invention, using which the codes used by the system are produced and compared.

DETAILED DESCRIPTION

Figure 1:
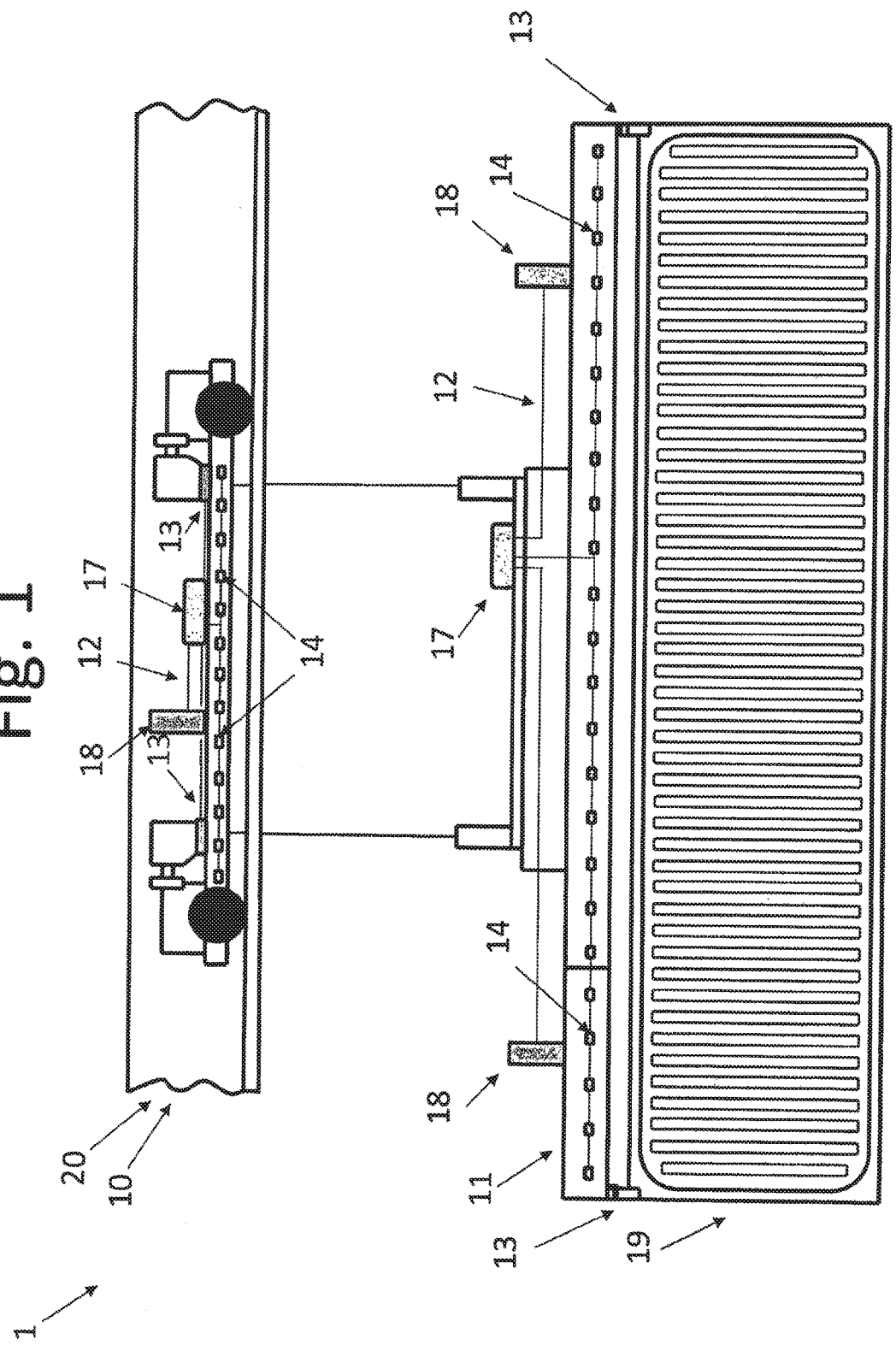
FIG. 1 shows parts of a system according to the invention, in which sensors and oscillation devices are adapted into a container handling device.

FIG. 1 shows a container security system (1) according to the invention and its parts. The system comprises the so-called lifting beam (11) of a container handling device (10). In the lifting beam (11) are installed force sensors (13) and acceleration sensors (14). The sensors (13) (14) are coupled to the electronics unit (17) of the system with conductors (12). Furthermore, to the electronics unit (17) of the system is connected a so-called oscillation device (18) with conductors (12). The oscillation device (18) is installed in the so-called lifting beam (11) of the container handling device. The sensors (13) (14) and oscillation devices (18) may be a plurality. From the electronics unit (17) of the system is a TCP/IP-based wireless connection to the computers of the system. To the computers of the system can be connected several container handling devices (10).

In one embodiment of the invention shown in FIG. 1, the sensors (13) (14), the electronics unit (17) of the system and the oscillation device (18) are installed in the frame (20) of the container handling device. Also in this embodiment, the sensors (13) (14) as well as the oscillation device (18) are coupled with conductors (12) to the electronics unit (17) of the system. In a solution according to the invention, the electronics unit (17) of the system controls the oscillation device (18) programmatically producing the forced oscillation of the container and the container contents (19). The programming commands and code files affecting control of the oscillation device are received from the computers of the system. The sensors (13) (14) measure the forces, oscillation forces and variations in force caused during the oscillation stage. The invention is thus directed to a system recognizing forced oscillation.

Figure 2:
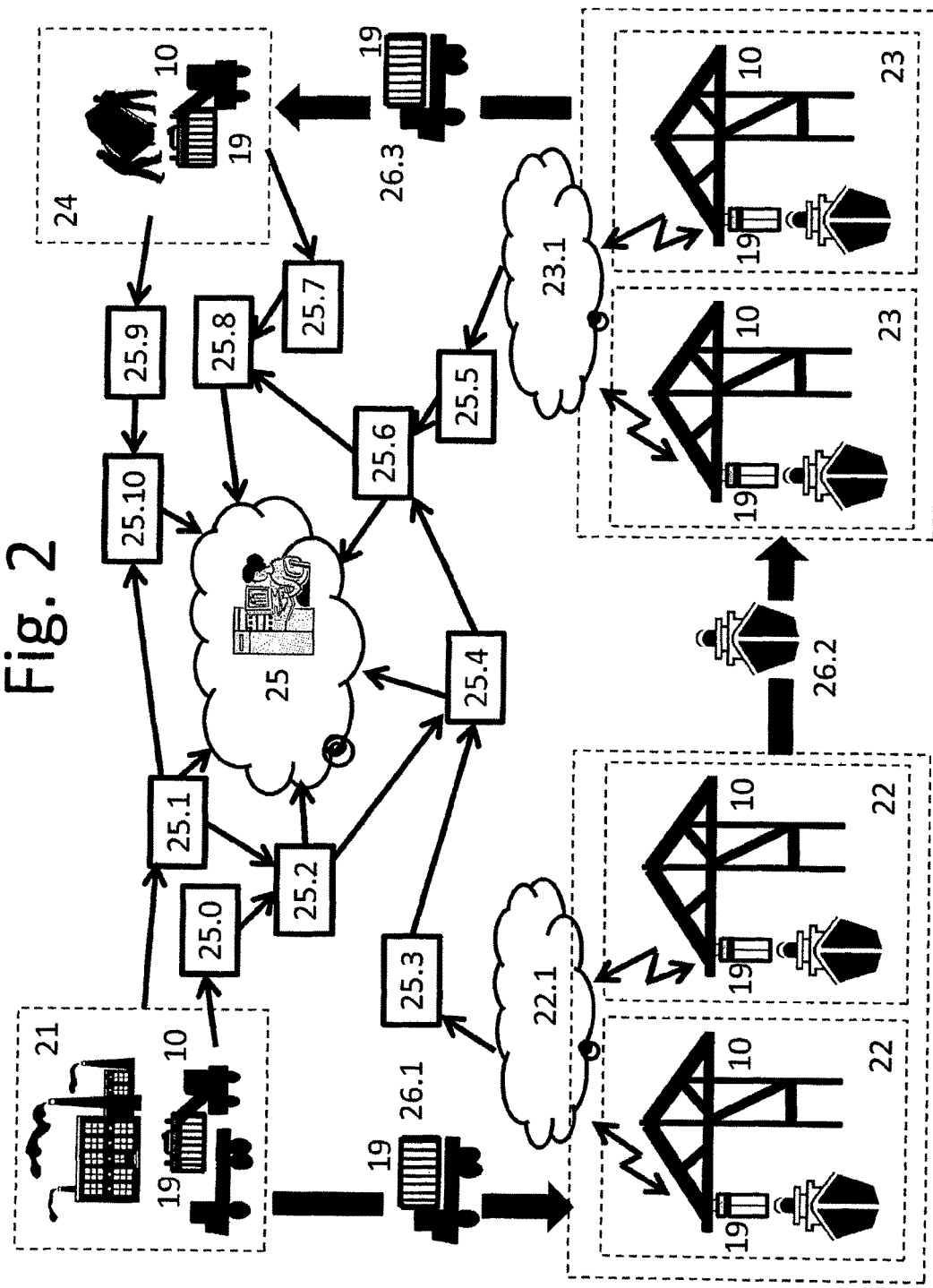
FIG. 2 shows parts of a system according to the invention, which are adapted to the system in one logistics chain.

In one embodiment of the invention shown in FIG. 2, the parts of the system are adapted to the system in one logistics chain. The container handling device (10) used by the invented system can be a harbour container crane, container straddle carrier, container telehandler, in other words all container handling devices, which lift the container (19) free of the ground, while the container is being moved (loading, unloading, storage). In addition to new container handling devices, a container security solution (system) following the invented method can also be retrofitted into all existing container handling devices.

In one embodiment of the invention shown in FIG. 2, the system recognizes in the container handling stage (21), while the container is being lifted or moved forward, the identifier of the container being handled and receives the departure information relating to the container. Next, the system produces using the oscillation device (18) of the telehandler of the facility a mechanical oscillation directed onto the container (19) and the contents. During the oscillation produced in the container handling stage (21), the system creates for the container, on the basis of signals received from the sensors (13) (14), its own container-specific code (25.0) based on forces, oscillation forces and variations in force and compares this to the code (25.1) retrieved from the database of the system (25). The code (25.1) is created before loading of the container on the basis of the oscillation measurement of the empty container. Thereafter, the system compares above said codes (25.0, 25.1) in the electronics unit (17). The result of the comparison can be an indication that inside above said container is a stowaway/stowaways. Additionally, the result can be an indication of deviation from the contents declared in advance in the freight information or an indication that the condition of the container contents according to the freight information or the condition of the container has changed. In a normal situation, the system gives indication of correct freight contents and safe condition of the container and informs of this to the user of the system. Thereafter, in the handling stage (21), the handled container (19) and its contents are inspected as well as secured with codes (25.0, 25.2) for the next handling stage (22). The codes (25.0, 25.2) are stored in the databases of the system. In this described stage of the embodiment, transportation (26.1) of the container is performed by road.

In one embodiment of the invention shown in FIG. 2, in the container handling stage (22) of the system (from the road to the sea), the system produces using the oscillation device (18) of the harbour crane a mechanical oscillation directed onto the container (19) and contents. During the oscillation produced in the container handling stage (21) of the harbour, the system creates for the container, on the basis of signals received from the sensors (13) (14), its own container-specific code (25.3) based on forces, oscillation forces and variations in force and compares this to the code (25.0) retrieved from the database of the system (25). Thereafter, the system compares above said codes (25.0, 25.3) in the electronics unit (17). The result of the comparison can be an indication that inside above said container is a stowaway/stowaways. Additionally, the result can be an indication of deviation from the contents declared in advance in the freight information or an indication that the condition of the container contents according to the freight information or the condition of the container has changed. In a normal situation, the system gives indication of correct freight contents and safe condition of the container and informs of this to the user of the system. Thereafter, in the handling stage (22), the handled container (19) and its contents are inspected as well as secured with codes (25.3, 25.4) for the next handling stage (23). In this described stage of the embodiment, transportation (26.2) of the container is performed by seaway.

In one embodiment of the invention shown in FIG. 2, the system performs the same kind of container handling methods in every stage of the logistics chain (21, 22, 23, 24).

In one embodiment of the invention shown in FIG. 2, the system performs the same kind of container handling method in the container handling stage (24) ending the logistics chain on the unloaded, empty container and creates for the container, on the basis of signals received from the sensors (13) (14), its own container-specific code (25.9) based on forces, oscillation forces and variations in force and compares this to the code (25.1) for the empty container retrieved from the database of the system (25).

In one embodiment of the invention shown in FIG. 2, using the system, it is possible to monitor indications based on the container codes (25.0-25.8), container handling stages (21, 22, 23, 24), container inspection results (25.2, 25.4, 25.6, 25.8, 25.10) and the progress of the container (26.1-26.3). Additionally, using the system, it is possible to plan and control container handling stages (21, 22, 23, 24), the inspection measurements of container handling devices (10) and comparisons.

In one embodiment of the invention shown in FIG. 2, the user(s) of the system place(s) in the user interface of the container handling device coupled to the system the user's own ID card before initiating use of the software and container handling device (10) of the system (25). The user interface of the system (25) prevents starting and use of the system (25) software, container handling device (10) or container handling devices (10), if above said ID card and/or identifier number is not placed in the user interface.

In one embodiment of the invention shown in FIG. 2, the results obtained by the electronics unit (17) of the system are conveyed and stored in the software of the system (25) and/or some other information system (22.1, 23.1) of the harbour operator by means of encrypted and wireless data transmission traffic. The software and user interface(s) of the system can alternatively be installed in the information system (22.1, 23.1) of the operator, a PDA/mobile device of the user or fixedly in the usage area of the container handling device. The software and the user interfaces of the system (25) are protected by the user's own ID card/reader and/or identifier number.

Figure 3:
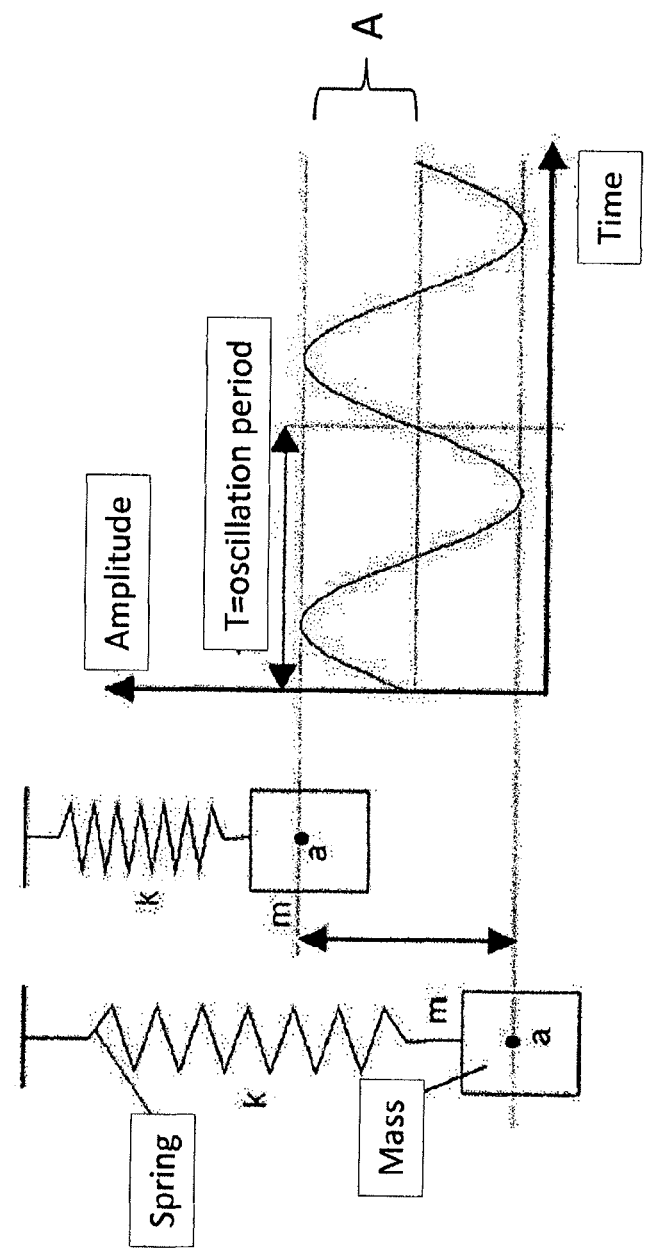
FIG. 3 shows parts and methods of a system according to the invention, which are adapted to analyse signals received from the sensors, and parts, which are adapted to control oscillation devices.

The embodiment of the invention shown in FIG. 3 shows in principle, how signals received from the sensors are analyzed and the oscillations of the container (19) are controlled. The oscillations of point a can be described by a simple spring-mass system. When mass m is momentarily affected by some outside force, it remains oscillating on both sides of its equilibrium position. In the system, a spring or spring constant k is an elastic item, in which force creates a given displacement. The time consumed by one oscillation is marked by the letter T. When the movement of the mass in relation to time is drawn in the coordinate system, the time signal is obtained.

In one embodiment of the invention shown in FIG. 3, the technology of the invention does not require the container's own oscillation or that of an intruder into the container or a change in the container or the container contents, instead the results to be presented are determined by comparing the changes in elasticity k of the object (container and/or container contents) to be measured. Above said elasticity k and the changes in elasticity k of the object to be measured are determined by measuring forced oscillation using acceleration- and force sensors installed into the container handling device and by analyzing the measurement results in the electronics unit of the device. The forced oscillation of the container (19) and the container handling device (10) is produced programmatically by stimulating with the oscillation device attached to the container handling device. An outside force, i.e. a so-called stimulus caused by forced oscillation, is produced with the oscillation device (18) programmatically, which can be periodic, randomly generated, produced according to a stored file or impact-like.

In one embodiment of the invention shown in FIG. 3, the signals received from the sensors are analyzed by comparing in the electronics unit (17) of the apparatus. When above said stimulus is brought into the system, it creates forced oscillation as determined by the stimulus. When the stimulus has ceased, the system is in its standard state, the oscillation of which can be free, unattenuated or free, attenuated oscillation. Comparison of the signal can occur during forced oscillation or during free oscillation. In the comparison, the time period (T) of the oscillation can be sought or a defined number of oscillations and the average of their amplitudes A or the time, in which stimulated oscillation falls below a defined limit value (A(t)). Furthermore, the comparison seeks to find a so-called virtual resonance between two moments of comparison, for example, between the departure harbour (22) and the arrival harbour (23) using the same object (container and/or container contents) to be measured. By resonance is meant that the same container (19) oscillates in the same manner at both moments of comparison, for example, in FIG. 2 the departure harbour (22) and the arrival harbour (23).

In one embodiment of the invention shown in FIG. 4, the codes used by the system are produced and compared. At the beginning, in the code is defined the ID of the code, which connects the code and the container. Next, in the code is defined the number of the container as well as the serial number (SN1) of the container. Next, in the code is defined the serial number (SN2) of the container handling device and the serial number (SN3) of the oscillation device of the container handling device. Next, in the code is recorded the temperature of the moment of oscillation from the lifting beam of the container handling device or as measured from the container using an infrared method. The three serial numbers SN1, SN2 and SN3 as well as the temperature t are used as comparison adjustment parameters in the oscillation comparison algorithm. Next, the code has the identifier for the control manner of the oscillation. Thereafter, the code has the time period (T) of oscillation measured at defined time point and the average value (ka) of the amplitudes A of oscillation measured at defined time point and the time, in which oscillation attenuates below a defined limit value (A (t)) and a percentage value (R) describing the quality of above said resonance.

It is obvious to the person skilled in the art that the invention is not limited to the embodiments presented above, rather many variations are possible within the scope of the accompanying claims. Features presented in the description possibly together with other features can, as needed, also be used separately from each other.

The invention claimed is:

1. A container security system comprising:
   force sensors and acceleration sensors attached to a lifting beam of a container handling device or to a frame of the container handling device;
   an oscillation device attached to the lifting beam of the container handling device or to the frame of the container handling device and arranged to create oscillation of a container during a container handling stage in which the container is empty; and
   an electronics unit arranged, during the container handling stage,
   (i) to generate a second code for the empty container based on elasticity of the empty container during the container handling stage, the elasticity being determined by measurement of the created oscillation by the force sensors and acceleration sensors and analysis of results of the measurement, and
   (ii) to recognize a change in a condition of the container by comparison of the second code to a first code, which is based on elasticity of the container when empty during a prior container handling stage, wherein
   the comparison of the first code and the second code does not require change of mass of the container.

2. The container security system according to claim 1, wherein:
   the electronics unit is configured to process force, oscillation and variations in force signals during the oscillation stage.

3. The container security system according to claim 1, wherein results obtained by the electronics unit are conveyed and stored in at least one of software of the container security system and another information system by way of encrypted and wireless data transmission traffic.

4. The container security system according to claim 1, wherein the container security system further comprises a user interface configured to present the results.

5. The container security system according to claim 1, wherein the force and the acceleration sensors, the electronics unit and the oscillation device are installed in the frame of the container handling device.

6. The container security system according to claim 1, wherein the electronics unit controls the oscillation device to programmatically produce forced oscillation of the container.

7. The container security system according to claim 1, further comprising a memory storing programming commands and code files affecting control of the oscillation device.

8. The container security system according to claim 1, wherein the container handling device is a harbor container crane, a container straddle carrier or a container telehandler.

9. The container security system according to claim 1, further comprising software and at least one user interface of the container security system that are installed in an information system of an operator, a PDA/mobile device of a user or fixedly in the vicinity of the container handling device.

10. The container security system according to claim 1, wherein:
during another container handling stage in which the container is loaded,
(i) the oscillation device is arranged to create oscillation of at least one of the container and container contents, and
(ii) the electronics unit is arranged to recognize a change in condition of the at least one container and container contents by comparison of elasticity of the at least one container and container contents to an elasticity of the at least one container and container contents obtained from a prior container handling stage in which the container is loaded; and
the comparison of the elasticities does not require change of mass of the at least one container and container contents.

11. A method for performing container handling with a container security system, the method comprising:
in a container handling stage of the container security system in which a container is empty, producing by way of an oscillation device a mechanical oscillation directed onto the empty container;
during the oscillation produced in the container handling stage, creating for the container, based on signals received from force sensors and acceleration sensors, a container-specific code based on elasticity of the container; and
during the container handling stage, comparing the container-specific code to another code that is based on elasticity of the container obtained from a prior container handling stage during which the container is also empty and that is retrieved from a database of the container security system,
wherein the comparison of the container-specific code and the other code does not require change of mass of the container.

12. The method according to claim 11, wherein the container security system compares the codes in an electronics unit.

13. The method according to claim 11, wherein the comparison allows determination of a virtual resonance between two moments at which the container oscillates in the same manner.

14. The method according to claim 11, wherein:
the container is handled in the container handling stage; and
in the container handling stage, the handled container is inspected as well as secured with codes for a next handling stage.

15. The method according to claim 11, wherein the container security system is arranged to monitor indications based on the container codes, container handling stages, container inspection results and progress of the container.

16. The method according to claim 11, further comprising:
during another container handling stage of the container security system in which the container is loaded, producing by way of the oscillation device a mechanical oscillation directed onto at least one of the container and container contents;
during the oscillation produced in the other container handling stage, creating for the container, based on signals received from the force sensors and acceleration sensors, another container-specific code based on elasticity of the at least one container and container contents; and
during the other container handling stage, comparing the other container-specific code to a code that is based on elasticity of the at least one container and container contents obtained from a prior container handling stage in which the container is loaded and that is retrieved from the database of the container security system,
wherein changes in the elasticity do not require change of mass of the at least one container and container contents.

* * * * *